United States Patent [19]

Sivard

[11] Patent Number: 5,355,894
[45] Date of Patent: Oct. 18, 1994

[54] METHOD FOR GENERATING A SIGNAL CORRESPONDING TO THE RESPIRATION VOLUME PER UNIT OF TIME OF A PATIENT

[75] Inventor: Ake Sivard, Solna, Sweden

[73] Assignee: Siemens Aktiengesellschaft, Munich, Fed. Rep. of Germany

[21] Appl. No.: 110,772

[22] Filed: Aug. 23, 1993

[30] Foreign Application Priority Data

Aug. 26, 1992 [EP] European Pat. Off. ........ 92114546.2

[51] Int. Cl.5 .......................................... A61B 5/0205
[52] U.S. Cl. ................... 128/725; 128/734; 607/9; 607/20
[58] Field of Search ............... 128/716, 723, 725, 734, 128/671; 607/6, 8, 9, 20

[56] References Cited

U.S. PATENT DOCUMENTS

| | | |
|---|---|---|
| 4,733,667 | 3/1988 | Olive et al. |
| 4,901,725 | 2/1990 | Nappholz et al. ................. 128/725 |
| 5,044,365 | 9/1991 | Webb et al. ....................... 607/20 |
| 5,137,019 | 8/1992 | Pederson et al. .................. 607/20 |
| 5,197,467 | 3/1993 | Steinhaus et al. ................. 607/20 |
| 5,201,808 | 4/1993 | Steinhaus et al. ................. 607/20 |

FOREIGN PATENT DOCUMENTS 0135911 4/1985 European Pat. Off. .
0310025 4/1989 European Pat. Off. .

OTHER PUBLICATIONS

"Methods of Filtering the Heart-Beat Artefact From the Breathing Waveform of Infants Obtained by Impedance Pneumography," Wilson et al., Med. & Biol. Eng. & Comp., vol. 20, No. 3, May 1992, pp. 293-298.

Primary Examiner—K. M. Pfaffle
Attorney, Agent, or Firm—Hill, Steadman & Simpson

[57] ABSTRACT

For generating a signal corresponding to the respiration volume per unit of time of a patient, a signal component correlated with the respiration is filtered out of a measured impedance signal acquired in the region of the heart of the patient, and the zero-axis crossings of this signal component are detected and the maximum values respectively arising in between two successive pairs of zero-axis crossings are identified in terms of amplitude. These maxima are added during a prescribed time interval to form a value corresponding to the respiration volume per unit of time.

3 Claims, 2 Drawing Sheets

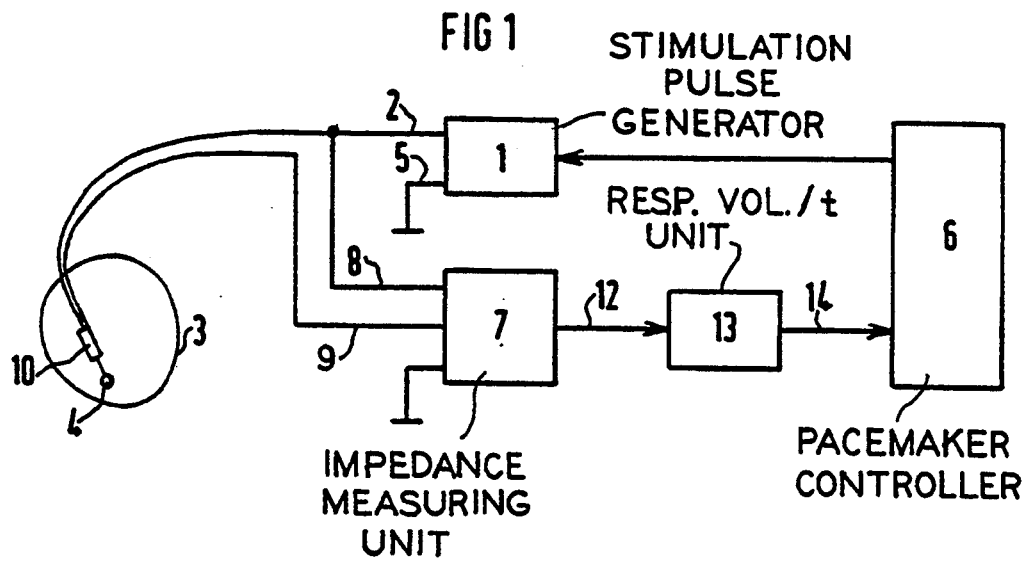
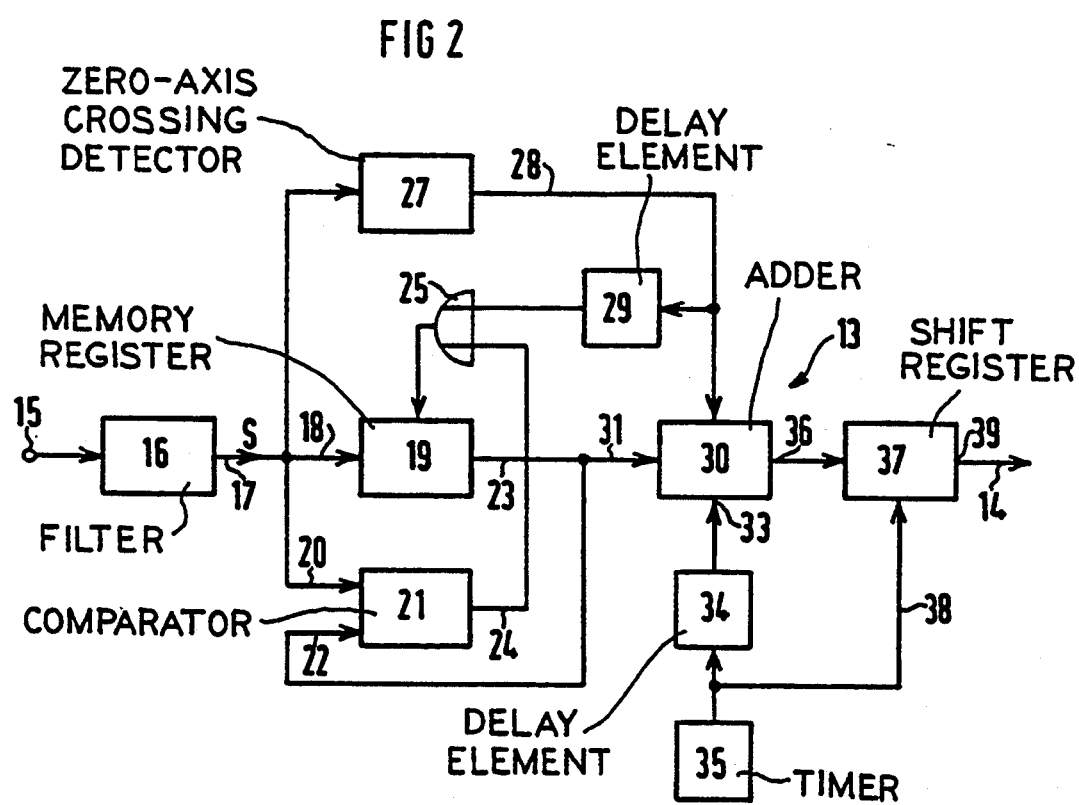

METHOD FOR GENERATING A SIGNAL CORRESPONDING TO THE RESPIRATION VOLUME PER UNIT OF TIME OF A PATIENT

BACKGROUND OF THE INVENTION

1. Field of the Invention

The present invention is directed to a method for generating a signal corresponding to the respiration volume per unit of time of a patient, of the type wherein a measured impedance signal is acquired with an electrode arrangement arranged in the region of the heart and a signal component correlated to the respiration of the patient is filtered out of the measured impedance signal and a selected characteristic of the filtered signal is analyzed to obtain a measurement of the respiration volume per unit of time.

2. Description Of the Prior Art

A method of this type is disclosed in U.S. Pat. No. 4,901,725, wherein a measured impedance signal of the heart of a patient is derived with an electrode arrangement of a heart pacemaker and with an impedance measuring means in the heart pacemaker, this measured impedance signal changing dependent on the pumping activity of the heart as well as dependent on intrathoracal pressure fluctuations externally acting on the heart and produced by the respiration and by movements of the patient. A signal component correlated to the respiration is filtered out of the measured impedance signal by band-pass filtering, with frequency parts of the measured impedance signal below 0.05 Hz and above 0.8 Hz are suppressed. Zero-axis crossings of the filtered-out signal component are detected with a zero-axis crossing detector, and a quantity dependent on the amount of the signal component is acquired at every zero-axis crossing, this quantity being utilized for the continuous formation of an average corresponding to the respiration volume per unit of time during a prescribed time interval. To this end, the signal component obtained by filtering is sampled and supplied to a zero-axis crossing detector as well as to an amplitude averaging unit. The amplitude averaging unit averages the amplitude of the samples over a duration corresponding to a few breaths to form an amplitude average of the signal component. It is assumed that the amplitude average of the signal component corresponds to the average volume per breath. At every detected zero-axis crossing during the course of the signal component, the momentary amplitude average of the signal component is supplied to a further averaging unit. This generates a further average value, based on the amplitude average of the signal component again identified at every zero-axis crossing, and that corresponds to the average volume per breath, according to the frequency of the zero-axis crossings that identify the respiratory rate. The further average thus corresponds to the product of volume per breath and respiratory rate, and thus to the respiration volume per time unit. The respiration volume per time unit identified in this way is utilized for the frequency control of the heart pacemaker.

As already mentioned, it is assumed in the known method that the amplitude average of the signal component that is filtered out of the measured impedance signal and is correlated to respiration corresponds to the average volume per breath. Such an assumption, however, is only true when the curve of the signal component is at least approximately sinusoidal and lies symmetrically relative to the zero line. In practice, however, the signal components, despite the filtering, are superimposed with signal parts that are based on the heart activity and on movements of the patient. These signal parts have in fact been reduced in signal height as a consequence of the filtering but can produce zero-axis crossings in the course of the signal component that are erroneously detected as inspiration or expiration of the measured impedance signal and are evaluated with the calculated value for the average volume per breath in the known method. A further source of error is that the lower limit frequency for the band-pass filtering of the measured impedance signal is fixed at an extremely low value, 0.05 Hz in the known method, in view of the lowest respiration rate to be anticipated, so that the zero line of the signal component can fluctuate considerably during the time required for the formation of the amplitude average of the signal component that corresponds to only a few breaths, and therefore the "real" zero line cannot be acquired. The formation of the amplitude of the signal component and their averaging therefore proceeds based on an artificially-set zero line, resulting in deviations of the artificially-set zero line from the real zero line lead to a constant which is not representative of respiration entering into the averaging, which is expressed as an error in the identification of the volume per breath.

SUMMARY OF THE INVENTION

It is an object of the present invention to provide a method which enables an adequately precise identification of the respiration volume per unit of time in an optimally simple way.

This object is achieved in accordance with the principles of the present invention in a method of the type initially cited wherein the maximum value of the amplitude of the filtered signal component which arises between two successive zero-axis crossings is acquired as a quantity dependent on the amplitude of the signal component. The sum of two successive maximum values of the amplitude of the signal component between successive pairs of zero-axis crossings (i.e., three successive zero-axis crossings) of the signal component corresponds to the degree of fluctuation of the signal component correlated with the respiration, and thus corresponds to the volume per breath of a breath. The position of the zero line selected for the identification of the amplitudes of the signal component is without significance for the result of the identification of the volume per breath, because a change in the position of the zero line leads to one maximum value being increased to the same extent as the other maximum value is decreased, so that the sum of the two maximum values, and thus the value for the volume per breath, remains constant.

Insofar as other signal parts that do not derive from respiration, but from heart activity or from movement of the patient, are superimposed on the signal component of the measured impedance signal that is correlated with respiration, the signal height of these signal parts is already substantially reduced due to the filtering of the measured impedance signal and therefore influences the identification of the respiration volume per unit of time to only a slight degree in the method of the invention. When, however, these signal parts disrupt the signal component in the area of the zero line, this can lead to additional detections of zero-axis crossings. According to the method of the invention for identifying the respiration volume per unit of time, however, the respective maximum values of the signal component between two successive zero-axis crossing pairs are utilized and since the disturbing signal parts are already considerably reduced with respect to their amplitude, the error in the identification of the respiration volume per unit of time that is thereby caused is only slight.

For forming the maximum value of the amount of the signal component between two zero-axis crossings in an embodiment of the method of the invention, samples of the amplitude of the signal component are supplied to a first input of a comparator whose second input is supplied with the content of a memory, and the current content of the memory is replaced by the current sample of the amplitude of the signal component when the amplitude of the signal component exceeds the value of the memory contents.

The formation of the average corresponding to the respiration volume per unit of time ensues in the simplest way in that the maximum values acquired during the prescribed time interval are summed in an adder.

DESCRIPTION OF THE DRAWINGS

FIG. 1 is a block circuit diagram of a frequency-controlled heart pacemaker which includes means for identifying the respiration volume per unit of time from a measured impedance signal derived from the heart operable according to the method disclosed.

FIG. 2 is a block circuit diagram of the means for identifying the respiration volume per unit of time shown in FIG. 1.

DESCRIPTION OF THE PREFERRED EMBODIMENTS

Figure 3:
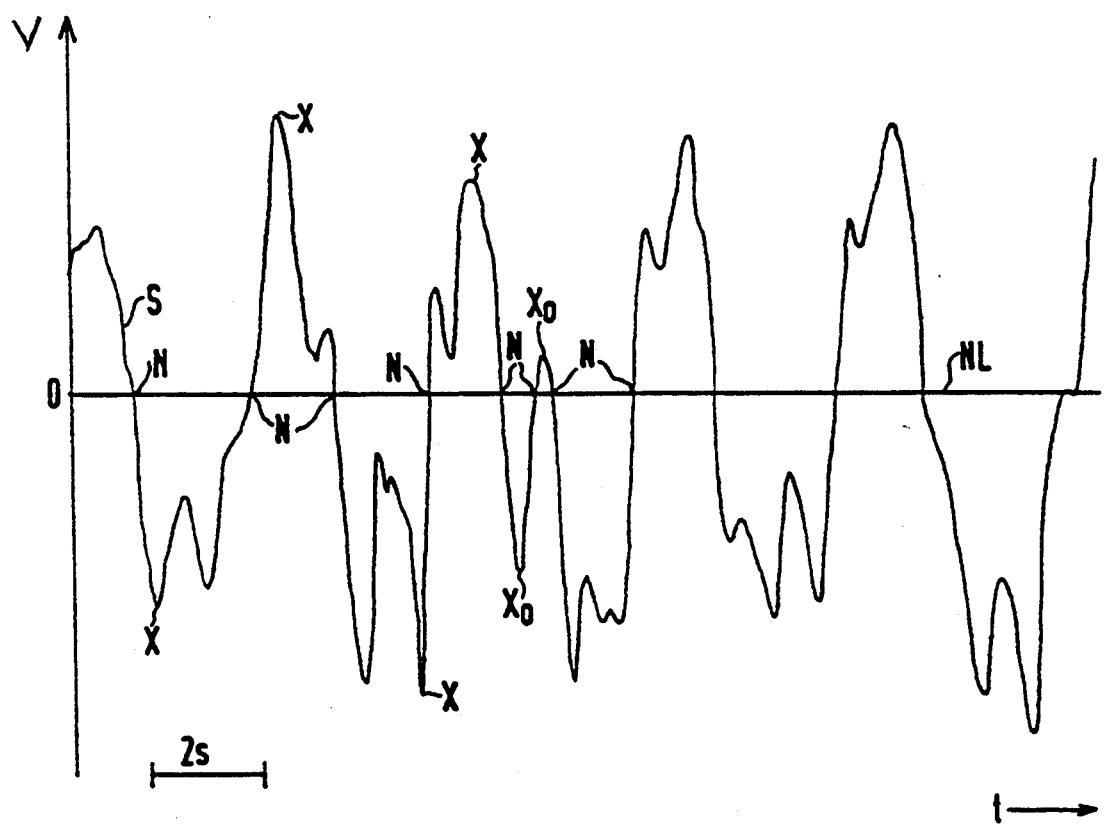
FIG. 3 shows an example for the curve of a signal component that is filtered out of the measuring impedance signal and which is correlated with respiration.

FIG. 1 shows the block circuit diagram of a heart pacemaker which includes a stimulation pulse generator 1 having a first output terminal 2, connected to a stimulation electrode 4 arranged in the heart 3 of the patient, and a second output terminal 5 connected to a housing of the heart pacemaker, which serves as cooperating (return) electrode for the stimulation electrode 4. For controlling the stimulation pulse output, the stimulation pulse generator 1 is connected to a heart pacemaker controller 6. An impedance measuring unit 7 has a test current output 8 connected to the stimulation electrode 4, a voltage measuring input 9 connected to an annular electrode 10 spaced from the stimulation electrode 4, and a reference terminal 11 connected to the housing of the heart pacemaker. The impedance measuring unit 7 generates a test current at prescribed times between the stimulation electrode 4 and the housing of the heart pacemaker, whereby the voltage drop produced by the test current in the region of the heart 3 between the stimulation electrode 4 and the annular electrode 10, or between the annular electrode 10 and the housing of the heart pacemaker is measured by the impedance measuring unit 7. The impedance measuring unit 7 generates a measured impedance signal at its output 12 that is supplied to a unit 13 for identifying the respiration volume per unit of time from the measured impedance signal (hence designated in FIG. 1 as resp. vol./t unit). The unit 13 has an output connected via a control line 14 to the heart pacemaker controller 6, which controls the stimulation pulse output dependent on the acquired respiration volume per unit of time.

FIG. 2 shows a block circuit diagram of the unit 13 for identifying the respiration volume per unit of time from the measured impedance signal. The unit 13 has an input charged with the measured impedance signal to which a filter arrangement 16 is connected. The filter arrangement 16 is essentially composed of a band-pass filter that has a passband from approximately 0.1 through 0.7 Hz and thus suppresses the signal parts of the measured impedance signal that do not correlate with the respiration and in particular are caused by the heart activity and by the movement of the patient. This signal suppression ensues incompletely, because extremely low heart beat frequencies or the frequencies of certain rhythmic movements of the patient can fall into the frequency range that is characteristic of the respiration of the patient. In order to be able to set the frequency passband of the band-pass filter as narrowly as possible, the center frequency of the band-pass filter is variable and is matched to the momentary respiration rate of the patient. The filter arrangement 16, further, is preferably fashioned as a digital filter so that a signal component S in the form of digitized samples that correlate with the respiration is present at the output of the filter arrangement 16, these samples being superimposed to a limited extent by signal parts produced by the heart activity and by the movement of the patient.

The filter arrangement 16 has an output 17 connected to the data input 18 of a memory register 19 and to a first input 20 of a comparator 21 whose second input 22 is connected to a data output 23 of the memory register 19. When the sample of the signal component S supplied to the first input 20 of the comparator 21 exceeds the value of the content of the memory register 19 present at the second input 22 of the comparator 21, the comparator 21 generates an output signal at an output 24 that is supplied via an OR element 25 to a control input 26 of the memory register 19, enabling acceptance of the sample of the signal component S present at the data input 18.

A zero-axis crossing detector 27 is connected to the output 17 of the filter arrangement 16. The detector 27 detects every change in operational sign in the digital samples of the signal component S and thereby generates a control signal at an output 28. In order to prevent changes in operational sign caused by noise signal parts of the signal component S being falsely detected as zero-axis crossings of the signal component S, the detection of the change in operational sign preferably ensues with a hysteresis. The output 28 of the zero-axis crossing detector 27 is connected via a delay element 29 and via the OR element 25 to the control input 26 of the memory register 19.

An adder 30 has a data input 31 connected to the data output 23 of the memory register 19 and has a control input 32 connected to the output 28 of the zero-axis crossing detector 27. Every time the zero-axis crossing detector 27 generates an output signal, the current memory content of the memory register 19 is accepted by the adder 30 and added to the aggregate value contained therein. The transferred memory content thereby corresponds to the maximum sample of the signal component S between the zero-axis crossings that was just detected and the zero-axis crossing that was detected before it. The adder 30 further has a reset input 33 to which a timer circuit 35 is connected via a further delay element 34. The timer circuit 35 generates an output pulse every five seconds. An averaging unit 37 in the form of a shift register is connected to the output 36 of the adder 30. This shift register is connected via a control line 38 to the timer circuit 35. The aggregate value at the output 36 of the adder 30 is transferred into the shift register 37 every five seconds and is added to a given plurality, for example, five, of the most recently transferred aggregate values. A continuous average of the respiration volume per unit of time during the most recent 30 seconds is thus formed in the shift register 37 in this way, which is supplied at the output 39 of the averaging unit 37 to the heart pacemaker controller 6 via the control line 14 (FIG. 1).

As FIG. 3 shows, the curve of the signal component S filtered out of the impedance signal deviates from an ideal, sinusoidal curve due to signal parts that arise from motion artifacts with frequencies in the range of the respiration rate. The zero-axis crossings N of the signal component S are detected with reference to a zero line NL in the unit 13 of FIG. 2 and the value X of the signal component S that is greatest in terms of amplitude is identified between two successive zero-axis crossings N. The sum of two such successively identified maximum values X thereby corresponds to the volume per breath, and the maximum values X summed during the prescribed chronological duration of five seconds in the adder 30 yield a measure for the respiration volume per unit of time.

As FIG. 3 also shows, the extreme values $X_O$ That are not related to the respiration can also enter into the identification of the respiration volume per unit of time; the influence of such disturbances on the identification of the respiration volume per unit of time, however, is quite slight due to their rare occurrence and due to the pre-filtering.

Although modifications and changes may be suggested by those skilled in the art, it is the intention of the inventor to embody within the patent warranted hereon all changes and modifications as reasonably and properly come within the scope of the inventor's contribution to the art.

I claim as my invention:

1. A method for generating a signal corresponding to the respiration volume per unit of time of a patient, comprising the steps of:
   acquiring a measured impedance signal from an impedance measuring system including an electrode arrangement disposed in a region of the heart of said patient;
   filtering a signal component out of said measured impedance signal correlated with the respiration of the patient, said signal component having a plurality of zero-axis crossings;
   detecting said zero-axis crossings of said signal component;
   identifying a maximum amplitude value of said signal component between each of two successive pairs of zero-axis crossings; and
   forming a continuously updated average of said maximum amplitude value over a predetermined time interval, said average corresponding to the respiration volume per unit of time of said patient.

2. A method as claimed in claim 1 wherein the step of identifying said maximum value of said signal component between successive zero-axis crossings is further defined by:
   sampling said signal component to obtain a sampled signal component signal;
   supplying said sampled signal component signal to a first input of a comparator;
   supplying a current content of a memory to a second input of said comparator and comparing said first input with said second input in said comparator; and
   replacing said current content of said memory with said sampled signal component signal if the amplitude of said sampled signal component signal exceeds said current memory content.

3. A method as claimed in claim 1 wherein the step of forming an average is further defined by adding a plurality of said maximum values obtained in a plurality of successive zero-axis crossings in an adder to obtain a sum corresponding to said respiration volume per unit of time.

* * * * *